United States Patent [19]

Haga

[11] Patent Number: 5,523,846

[45] Date of Patent: Jun. 4, 1996

[54] APPARATUS FOR DETECTING MARKS FORMED ON A SAMPLE SURFACE

[75] Inventor: Kazumi Haga, Chofu, Japan

[73] Assignee: New Creation Co., Ltd., Tokyo-to, Japan

[21] Appl. No.: 346,166

[22] Filed: Nov. 21, 1994

[51] Int. Cl.⁶ .................. G01B 11/30; G01N 21/55
[52] U.S. Cl. .................. 356/445; 356/371; 359/606
[58] Field of Search ................. 356/445, 371; 359/602, 606

[56] References Cited

U.S. PATENT DOCUMENTS

| | | | |
|---|---|---|---|
| 3,815,998 | 6/1974 | Tietze | 356/371 |
| 4,346,996 | 8/1982 | Miller | 356/243 |
| 4,428,670 | 1/1984 | Ruell et al. | 356/71 |
| 4,907,858 | 3/1990 | Hara et al. | 359/602 X |

*Primary Examiner*—Vincent P. McGraw
*Attorney, Agent, or Firm*—Evenson, McKeown, Edwards & Lenahan

[57] ABSTRACT

An apparatus for inspecting the surface condition of an object comprises a light source, an optical element for directing irradiating light from the light source to an object and for converging the light reflected by the surface of the object at its back focal plane to form an image behind the back focal plane, and an observing apparatus for observing the image. An aperture stop is arranged at or near the back focal plane to cut off a scattered component of the reflected light. A half mirror having two planes forming a predetermined micro angle each other deflects the reflected light from the optical path of the irradiating light.

4 Claims, 6 Drawing Sheets

| stop diameter(mm) | condition 1 | condition 2 | condition 3 |
|---|---|---|---|
| .5 | 12.6196 | 8.2899 | 6.20975 |
| 1 | 25.2392 | 16.5798 | 12.4195 |
| 1.5 | 37.8588 | 24.8697 | 18.6293 |
| 2 | 50.4784 | 33.1596 | 24.839 |
| 2.5 | 63.0979 | 41.4495 | 31.0488 |
| 3 | 75.7175 | 49.7394 | 37.2585 |
| 3.5 | 88.3371 | 58.0293 | 43.4683 |
| 4 | 100.957 | 66.3192 | 49.678 |
| 4.5 | 113.576 | 74.6091 | 55.8878 |
| 5 | 126.196 | 82.899 | 62.0975 |

APPARATUS FOR DETECTING MARKS FORMED ON A SAMPLE SURFACE

BACKGROUND OF THE INVENTION

1. Field of the Invention

The present invention relates generally to an apparatus for inspecting the surface condition of an object, and more particularly to an inspection apparatus suitable for detecting marks formed on the sample surface.

2. Description of Background Art

Heretofore, it is known an inspection apparatus using the Schlieren optical system for detecting a surface condition (e.g. waviness, dimples, projections, cleaning imperfection, buff damages etc.) of mirror wafers or the like used for manufacturing semiconductor integrated circuits. The Schlieren optical system is described, for example, in a publication "NEEDS AND SEEDS FOR OPTICAL MEASUREMENT" (Measure-control association corporation/ Reserch study committee for the application of light to measurement technology, 1990, The Corona Inc.).

The Schlieren optical system is one of representative systems for indicating variations of the refractive index and the reflectivity due to the irregularity of a sample surface as differences in brightness. In this optical system, light from a point source is converted into collimated light via an optical element (lens), the collimated light is irradiated to the sample surface perpendicularly thereto, then the light reflected thereby is converged via an optical element (lens), and finally a reflected image is observed by the naked eye, a camera or the like behind the knife edge.

According to this optical system, when reflected by the sample surface the light is scattered at a portion of the sample surface having irregularities thereon, and the scattered component of the reflected light impinged on the knife edge is cut off. As the result of which, a portion of the image corresponding to the scattered component cut off by the knife edge becomes dark behind the knife edge, and the other portion becomes bright. Since this light/dark (i.e. brightness) pattern corresponds to the surface condition of the sample, it is possible to observe the surface condition of the sample.

By the way, in the Schlieren optical system wherein any knife edge is not used and thereby no scattered component is cut off, since the whole image becomes bright, the observation is carried out by obtaining a bright/dark pattern having small quantity of light. There is therefore a problem that the light/dark pattern is very hard to observe for lack of its contrast.

On the other hand, it is known another type of such a Schlieren optical system which has not any knife edge and in which the observation of a surface condition of a sample is carried out at a selected region having a relatively high contrast by setting its focus slightly off the point.

However, these inspection apparatus of the prior art have following problems.

That is, in the inspection apparatus using the former type Schlieren optical system, although it is possible to obtain a light/dark pattern corresponding to the surface condition of the sample behind the knife edge, the contrast of the light/dark pattern is low since it contains much scattered component which passes through the opposite side of the knife edge and therefore cannot be cut off by it. In addition, since the range which can be observed behind the knife edge is part of the sample surface and not the whole thereof, the sample should be turned one revolution around its optical axis in order to observe the whole sample surface.

On the other hand, in the inspection apparatus using the latter type Schlieren optical system in which the observation plane is moved along the optical axis, the contrast obtained is very low. In addition, although it is possible to vaguely discriminate an area including irregularities, it is impossible to clearly discriminate the magnitude of the depth and height of the area.

SUMMARY OF THE INVENTION

It is therefore an object of the present invention to provide an inspection apparatus which can exactly observe the surface condition of an object at a real time.

For achieving this object, there is provided, according to the present invention, an apparatus for inspecting the surface condition of an object comprising a light source; an optical element having a back focal plane for directing irradiating light from said light source to the object and for converging the light reflected by the surface of the object at the back focal plane to form an image behind the back focal plane; a half mirror having two planes forming a predetermined micro angle each other for deflecting the reflected light from the optical path of the irradiating light; an aperture stop arranged at or near the back focal plane for cutting off a scattered component of the reflected light; and observing means arranged behind the back focal plane for observing the image.

According to the apparatus of the present invention, a returned component of the reflected light reflected by the surface of the object in a direction opposite to the incident direction passes through the aperture stop arranged at or near the back focal plane of the optical element, and almost all of a scattered component of the reflected light reflected by the surface in other directions is cut off by the aperture stop. Accordinly, a two dimensional light/dark pattern is formed behind the aperture stop by the returned component of the reflected light. This light/dark pattern represents the condition of irregularity and reflectivity and the like of the surface of the object, and thus provides a quick observation of the two dimensional condition of the surface. In this case, since the observation can be carried out with setting the focus on the point as well as almost all of the scattered component can be cut off, the visibility of the obtained light/dark pattern is remarkably improved. In addition, since there is provided the predetermined micro angle between two planes of the half mirror, it is possible to sufficiently deflect undesirable ghost light formed by one of the two planes from the optical axis of the aperture stop, and thus to remove the ghost light from the light/dark pattern formed behind the aperture stop.

DESCRIPTION OF THE PREFERRED EMBODIMENTS

A preferred embodiments of an inspection apparatus of the present invention will be hereinafter described with reference to the accompanying drawings.

Figure 1:
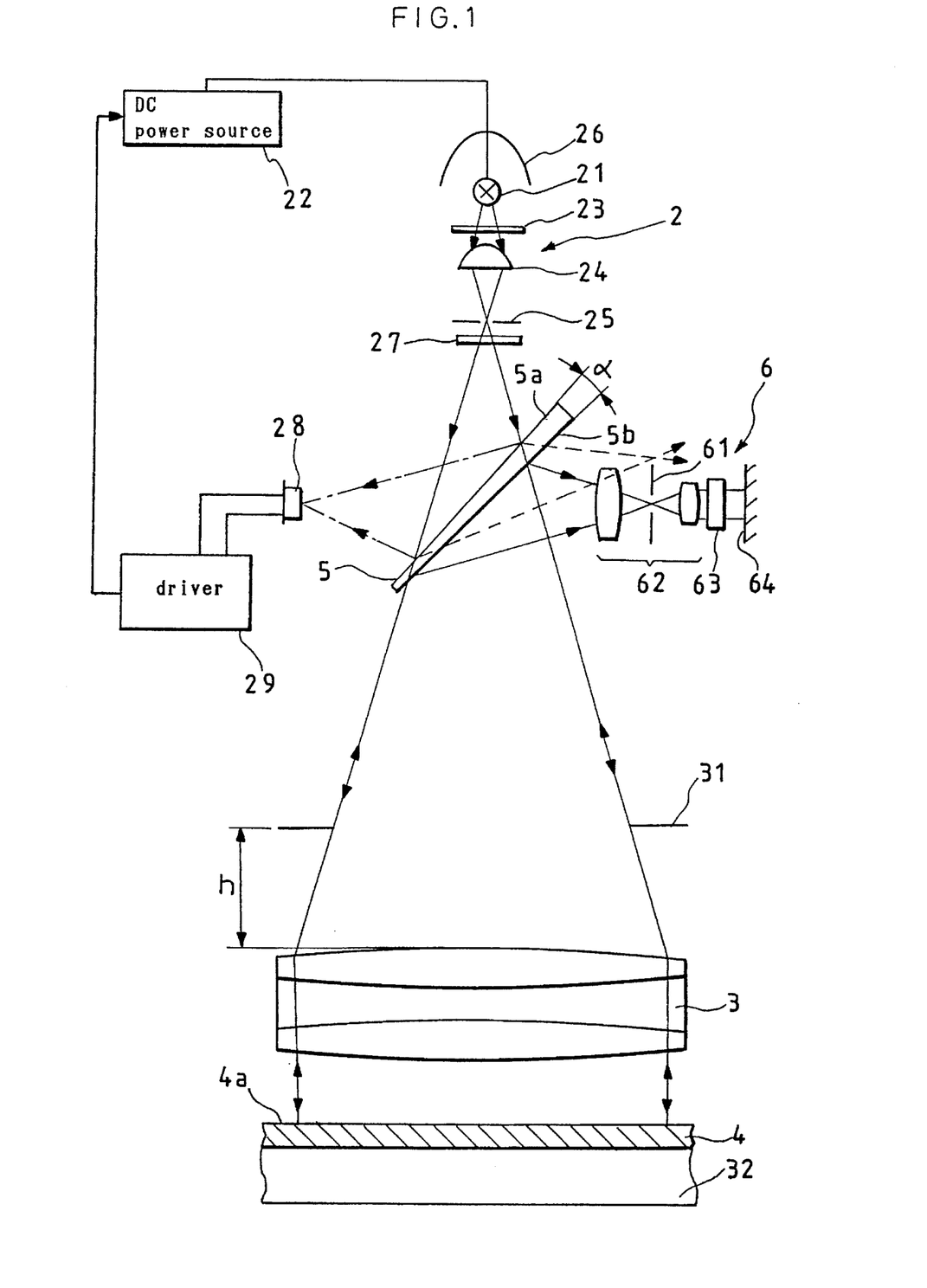
FIG. 1 is a schematic view of a preferred embodiment of an inspection apparatus according to the present invention.

FIG. 1 shows an inspection apparatus of a preferred embodiment of the present invention. First of all, the whole structure of the inspection apparatus will be generally explained. Irradiating light from a light source apparatus 2 is directed perpendicularly onto a surface 4a of a plate-shaped sample 4 (hereinafter reffered to "sample surface 4a") after being collimated by a collimator lens 3. The light is reflected by the sample surface 4a, travels in a direction opposite to that of the irradiating light, and converged by the collimator lens 3 and finally detected as an image by a detecting apparatus 6 after being deflected by a wedge-type half mirror 5 from the optical path of the irradiating light. The detecting apparatus 6 has an aperture stop 61 arranged at a position corresponding to a back focal plane of the collimator lens 3.

The operation of this apparatus will be briefly described. The presence of the aperture stop 61 in the detecting apparatus 6 enables almost all of a scattered component of the reflected light reflected not-perpendicularly by the sample surface 4a to be cut off, whereby clear image can be formed behind the aperture stop 61 by a returned component of the reflected light (i.e. regularly reflected light) reflected by the sample surface 4a perpendicularly thereto. Since the light/dark pattern of this image represents a condition such as irregularity and the like of the sample surface 4a, it is possible to observe a two dimensional distribution of micro variations of the condition of the sample surface 4a by watching the image output of the detecting apparatus 6. In addition, since the half mirror 5 is wedge-type, it is possible to deflect or remove undesirable ghost light formed by the transmission surface of the half mirror 5 from the optical axis.

Then the operation of the inspection apparatus of FIG. 1 will be described more in detail.

The light source apparatus 2 uses 100 W or 150 W halogen lamp 21 as a light emitting source thereof. The output of the halogen lamp 21 is controlled by a DC power source 22. The emitted light from the halogen lamp 21 is converged at a pinhole 25 having a diameter of 2 mm through a condenser lens 24 after being transmitted through a heat absorbing filter 23. Light emitted from back side of the halogen lamp 21 is also directed to the pinhole 25 through the condenser lens 24 after being reflected by an elliptical reflector 26 comprising a dichroic mirror. The pinhole 25 forms a point source of the irradiating light for illuminating the sample surface 4a. There is provided a turret-type wavelength selecting filter 27 including various interference filters which enable appropriate change of the wavelength of the irradiating light for illuminating the sample surface 4a. This wavelength selecting filter 27 is used for adjusting the sensitivity of the optical system portion of the inspecting apparatus, and a short wavelength region is selected for a small peak-to-valley of the irregularity of the sample surface 4a.

Part of the irradiating light from the light source apparatus 2 is reflected by the wedge-type half mirror 5, and then directed to a photodiode 28 through an appropriate lens (not shown). Photoelectric current detected by a driver 29 of the photodiode 28 is fed back as a control signal to the DC power source 22 so as to keep the luminance of the halogen lamp 21 constant.

The irradiating light from the light source apparatus 2 transmitted through the wedge-type half mirror 5 enters the collimator lens 3 after passing through an aperture 31. The collimator lens 3 has a function of converting the irradiating light from the pinhole 25 of the light source apparatus 2 into collimated light, and of directing it to the sample surface 4a. That is, the collimator lens 3 is so positioned that the position of the front focal plane thereof corresponds to the position of the pinhole 25. The collimator lens 3 is a 3-piece set of apochromat made of special low dispersion glass, and any one of three types of collimator lenses 3 having a diameter of 4 inch (F 9.5), 6 inch (F 7.1) and 8 inch (F 8.0) can be selectively used in accordance with the width of the observation region or the like.

The sample 4 to which the collimated light is irradiated is laid on a tilt-stage 32 which can fine control the inclination of the sample 4 so that the collimated light may be irradiated perpendicularly to the sample surface 4a. Light reflected by the sample surface 4a enters again the collimator lens 3 and its beam diameter is converged. During this period, the reflected light having a large scattering angle is cut off by the aperture 31. The diameter of the aperture 31 is 96 mm, 144 mm and 190 mm for the collimator lens 3 of 4 inch, 6 inch and 8 inch, respectively. A distance "h" between the top end of the collimator lens 3 and the aperture 31 is 117 mm, 118 mm and 154 mm for the collimator lens 3 of 4 inch, 6 inch and 8 inch, respectively.

The reflected light of which beam diameter is converged by the collimator lens 3 is dircted to the half mirror 5, and deflected by the half mirror 5 at a right angle relative to the optical path of the incident light so as to be separated therefrom. The half mirror 5 is a plate-shaped beam splitter, however, it is a special beam spritter in which a predetermined micro angle "α" is formed between two planes. Accordingly, ghost light (shown by dotted lines in FIG. 1) generated by the reflection at the upper transmission surface 5a gets off from the optical path of the desirable reflected light generated by the lower reflecting surface 5b, and cannot be detected by the detecting apparatus 6. The micro angle "α" is so determined that the ghost light does not enter the detecting apparatus 6 (e.g. the ghost light is cut off by an entrance diaphragm of a camera lens 62). Since error factors are increased as the micro angle "α" increases, it is preferable to make the micro angle "α" as small as possible so far as the ghost light is sufficiently cut off by the aperture stop 61. In consideration of these reasons, the micro angle "α" is set at one degree (1°) in the half mirror 5 of the preferred embodiment.

The reflected light deflected by the half mirror 5 enters the camera lens 62 arranged in the detecting apparatus 6. The camera lens 62 is a zoom lens and is adapted to use one of two types of focal lengths of 10–100 mm (F 1.4) and 9.5–152 mm (F 1.8) at need. An aperture stop 61 is arranged at a converging position within the camera lens 62. That is, the aperture stop 61 is arranged at a position corresponding to a back focal plane of the collimator lens 3. Accordingly, almost all of a scattered component of the reflected light from the sample surface 4a is cut off by the aperture stop 61. This aperture stop 61 is an iris stop comprising 10 blades, and is adapted to continuously change the diameter of the circular stop by moving its movable controller. An image suitable for each type of inspection (such as inspections for waviness, dimple or damage etc.) can be obtained by changing the diameter of the circular aperture.

Light from the camera lens 62 is projected onto a CCD 64 comprising 410,000 picture elements through an extender lens 63 having a magnification of two (2). An image signal from the CCD 64 is successively displayed on a monitor (not shown) as a reconstructed image after being converted into an electric signal, and processed by an appropriate signal processor. The image projected onto the CCD 64 is a two dimensional light/dark pattern corresponding to the condition of the sample surface 4a.

In more detail, the light/dark pattern of the image projected onto the CCD 64 is formed only by the returned component passed through the aperture stop 61 of the reflected light from the sample surface 4a. That is, almost all of the scattered component that is not perpendicularly reflected by the sample surface 4a is cut off by the aperture stop 61, and on the contrary, the returned component that is perpendicularly reflected by the sample surface 4a passes through the aperture stop 61. In addition, each position in the light/dark pattern formed by such returned component corresponds one-to-one to each position in the sample surface 4a. Accordingly, the light/dark pattern of the image projected onto the CCD 64 represents micro variations such as irregularlities on the sample surface 4a, and thus a two dimensional distribution of the micro variations of the sample surface 4a can be exactly observed.

Then theoretical analysis will be carried out using a simplified model in order to clarify the detecting performance of the detecting apparatus of the preferred embodiment of the present invention.

Figure 2:
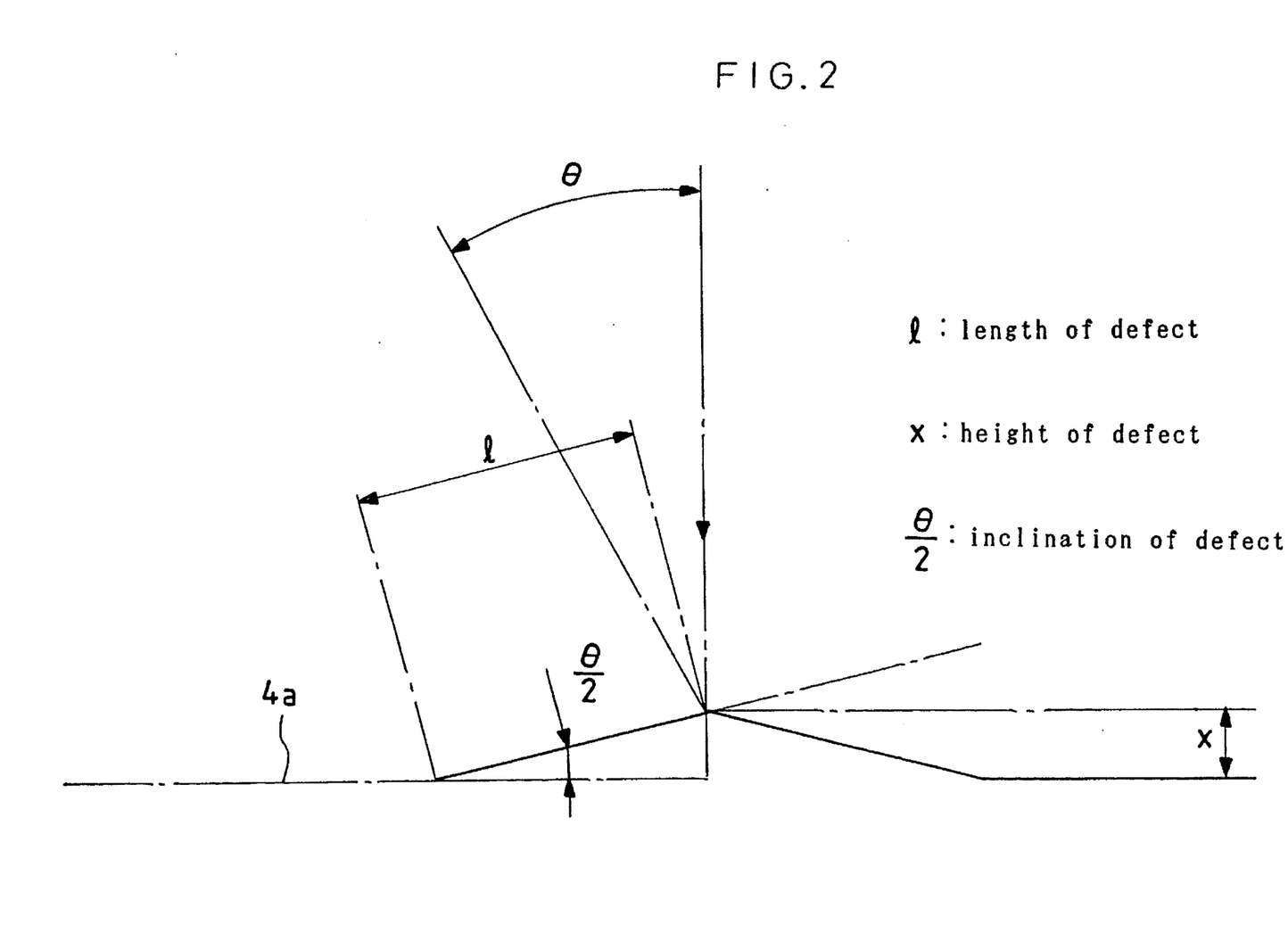
FIG. 2 is a schematic view of a cross-sectional model of a sample surface to be observed by the inspection apparatus according to the present invention.

FIG. 2 is a schematic view showing a cross-sectional model of a surface to be detected. FIG. 2 shows an example of the sample surface 4a having an even reflectivity and part of which is formed with defects each having a cross-section of an angled projection. The length, height and inclination of the defect are denoted by "l", "x" and "θ/2", respectively. If the defect is that of detection limit, the reflected light emitted from the defect of the sample surface 4a at an angle "θ" relative to the normal line to the sample surface 4a passes through the edge of the aperture stop 61. Accordingly, the angle "θ" can be defined as follows;

$$\theta = w/f \tag{1}$$

wherein "2 w" is the diameter of the aperture stop 61, and "f" is the focal length of the collimator lens 3. It is assumed that the collimator lens 3 and the sample surface 4a are arranged close to each other. Using the height "x" and the length "l" to eliminate "θ" from the equation (1), the equation (1) is transformed to a following equation;

$$x = wl/2\, f$$

Accordingly, the equation above is expressed as follows in a micro region;

$$\Delta x = \Delta w \cdot \Delta l / 2\, f \tag{2}$$

On the other hand, when designating the number of the aperture as "NA" and the resolving power as "N" of the collimator lens 3, the resolving power φ can be expressed as followings;

$$\phi = 1/N = 1.22 \lambda / 2n \cdot NA \tag{3}$$

wherein "n" is the refractive index and "λ" is the wavelength of the inspection light. Since "θ" is a micro angle, "φ" can be regarded as Δl. Accordingly, the micro height Δx of the defect can be expressed from the equations (2) and (3) as follows;

$$\Delta x = \eta \cdot (1.22\, \lambda/4\, f\, NA) \cdot \Delta w \tag{4}$$

Wherein "n"=1, and "η" is an illumination distribution error. If using "φ" denoting the diameter of the aperture stop 61, the equation (4) can be transformed as followings;

$$\Delta x = \eta \cdot (1.22\, \lambda/8\, f\, NA) \cdot \Delta \phi \tag{5}$$

Figure 3:
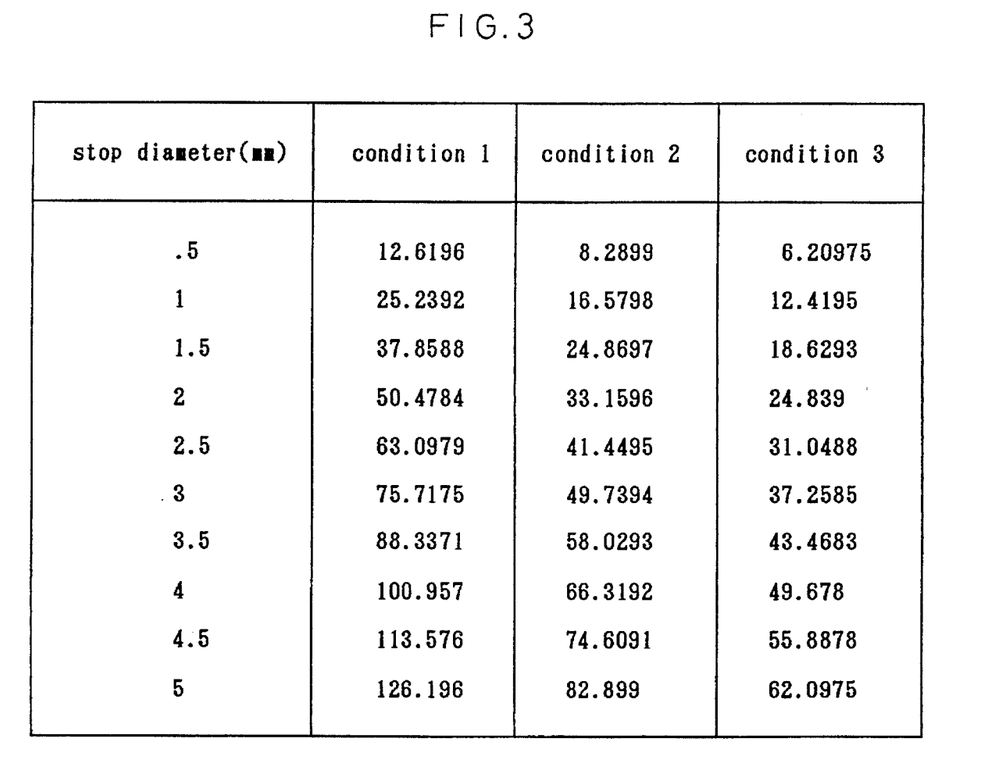
FIG. 3 is a table showing simulation results obtained with the use of the model of FIG. 2.

Results of the simulation using the equation (5) are shown in a table of FIG. 3. In this simulation, the micro height Δx of the defect i.e. the height of the detection limit (Å) was calculated with changing the aperture diameter Δφ in accordance with following three conditions. That is, in a first condition, the diameter of the collimator lens 3 is 100 mm and the focal length thereof is 640 mm. In a second condition, the diameter of the collimator lens 3 is 152 mm and the focal length thereof is 1368 mm. And in a third condition, the diameter of the collimator lens 3 is 203 mm and the focal length thereof is 1624 mm. In common with these all conditions, the wavelength "λ" of the inspection light is 550 nm and the illumination distribution error η is ½ (50%).

As shown in the table of FIG. 3, it can be seen that the detection limit height decreases in proportion to the decrease of the stop diameter. In addition, it can be seen that the detection limit height decreases in inverse proportion to the increase of the diameter of the collimator lens 3.

In the practical experiment using the inspection apparatus of the illustrated embodiment, it is confirmed that a detection exhibiting the result of the simulation can be obtained within a range of 4–5 mm of the stop diameter Δφ.

While the present invention has been described above in the form of a concrete embodiment thereof, it should be understood that the present invention is not limited to the illustrated embodiment and that those skilled in the art will be able to make various modifications and additions without departing from the scope of the present invention.

For example, the position of the light source apparatus 2 and the position of the detecting apparatus 6 can be exchanged with each other. That is, it may be possible to form the inspecting apparatus so that the irradiating light from the light source apparatus 2 is directed to the collimator lens 3 through the deflection by the wedge-type half mirror 5, and the reflected light reflected by the sample surface 4a and converged by the collimator lens 3 is directed to the detecting apparatus 6 having the aperture stop 61 after being transmitted through the wedge-type half mirror 5.

In addition, although in said preferred embodiment the half mirror 5 is disposed between the light source apparatus 2 and the collimator lens 3, it may be possible to arrange the half mirror 5 between the collimator lens 3 and the sample 4. In this case, a separate collimator lens is required in order to converge the reflected light deflected by the half mirror 5 at a position of the aperture stop 61 of the detecting apparatus 6.

Furthermore, although the halogen lamp 21 is used as the light emitting source of the light source apparatus 2 in said embodiment, it may be possible to use a xenon lamp or the like. The type of the light emitting source is determined based on the nature of the object to be inspected (sample 4). For example, when inspecting an object having a relatively high reflectivity such as a semiconductor wafer, either the halogen lamp or the xenon lamp may be used. On the contrary, when inspecting an object having a relatively low reflectivity such as a glass substrate, it may be preferable to use the xenon lamp having high luminance. Accordingly, it may be possible to provide a structure which enables an exchange of the light emitting source in accordance with the nature of the object to be inspected.

In addition, although the condenser lens 24 is incorporated in the light source apparatus 2 in said embodiment, it is possible to omit the condenser lens 24. In this case, the halogen lamp 21 is disposed at one focal point of the elliptical reflector 26, and the pinhole 25 is disposed at the other focal point. As the result of which, the same condition can be obtained as the case in which the point source would be arranged at the converging point since light reflected by the elliptical reflector 26 is converged at the pinhole 25 according to the nature of the ellipse. A parabolic reflector may be substituted for the elliptical reflector 26. In this case, it is preferable to provide a separate collimator lens for converging light at the pinhole since the light emitted from the parabolic reflector travels parallel to the optical axis.

Figure 4:
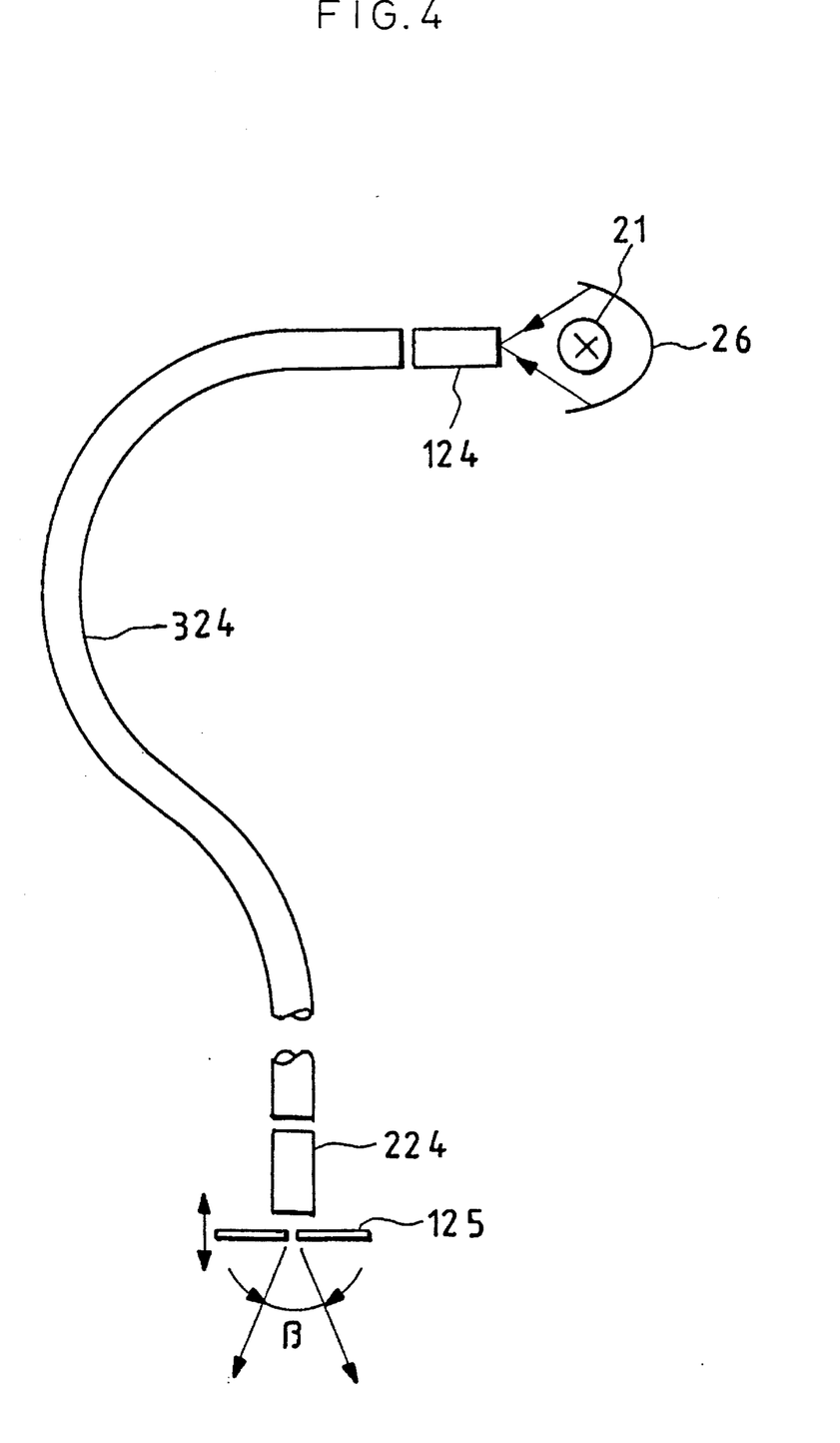
FIG. 4 is a schematic view of a modified embodiment of the light source apparatus of FIG. 1.

Furthermore, as shown in FIG. 4, it may be possible to form the light source apparatus 2 with the use of rod lenses 124 and 224 and a light guide fiber 324. In this case, the halogen lamp 21 is disposed at one focal point of the elliptical reflector 26, and one end of the rod lens 124 is disposed at the other focal point of the elliptical reflector 26. Emitting light from the halogen lamp 21 is led to one end of the light guide fiber 324 via the rod lens 124, and led to the rod lens 224 disposed close to the other end of the light guide fiber 324 passing therethrough. Light emitted from the rod lens 224 is converged at the aperture of a stop 125 forming a point source. It is necessary to match the divergent angle "β" of the irradiating light from the aperture of the stop 125 to the field angle of the collimator lens 3, which would be achieved by adjusting a distance between the rod lens 224 and the stop 125.

It may be also possible to use a photoconductive rod having a circular cross-section and made of the same glass as that forming the core of the light guide fiber 324 instead of using the rod lenses 124 and 224. The arrangement of the photoconductive rod at opposite ends of the light guide fiber 324 enables the emitted light from the halogen lamp 21 to be led to the light guide fiber 324 as well as the irradiating light passed through the aperture of the stop 125 after being transmitted through the light guide fiber 324 to be diverged at a large angle.

Figure 5:
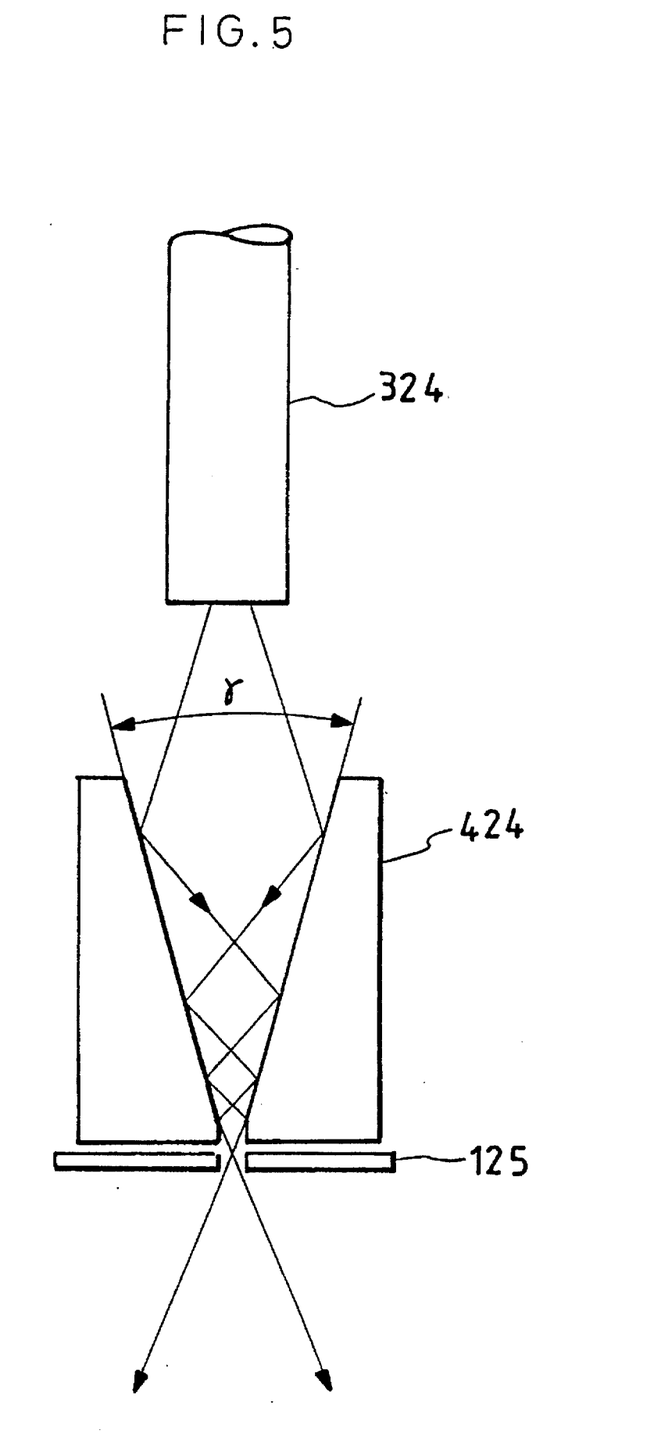
FIG. 5 is a schematic view of a further modified embodiment of the light source apparatus of FIG. 1.

In addition, it may be possible to have a structure of FIG. 5 in which the rod lens 224 in FIG. 4 is substituted for a conical mirror 424. In this case, emitted light from the light guide fiber 324 is converged at the aperture of the stop 125 by the conical-mirror 424. The diverging angle "γ" of the conical mirror 424 is determined based on the field angle of the emitting light from the light guide fiber 324 in order to prevent the light from being returned. In practice, the diverging angle "γ" of the conical mirror 424 is about 9°.

It may be also possible to form a further separate light source apparatus in which the collimator lens 3 can be directly irradiated with light emitted from tile output end of the light guide fiber 324 without using the rod lens 224.

Furthermore, the pinhole 25 for forming the point source may be substituted for a slit. In this case, it is possible to widen the emitting angle of the irradiating light from the light source.

In addition, although the interference filter is used as the wavelength selecting filter 27 in said embodiment, it may be possible to use a colored glass filter. The wavelength selecting filter 27 is not always necessary and it may be disposed below the half mirror 5.

In addition, although only the wavelength selecting filter 27 is used in said embodiment, it may be possible to use an ND filter together with or in stead of the wavelength selecting filter 27. The ND filter is used for the purpose of light reduction without changing the spectral characteristics of the incident light. The light reduction will be required for detecting e.g. the waviness or the like of the sample surface 4a, since the luminance of the sample surface 4a would be too excessive to observe a gentle surface variation such as waviness due to an extreme increase of the regular reflecting components of light. In this case, although the halogen lamp 21 may be substituted for a less luminous lamp, a simpler work may be carried out by the ND filter.

Furthermore, although the apochromat lens is used as the collimator lens 3 in said embodiment, it may be possible to use an achromat lens. When using narrow-band monochromatic light, the achromat is not always required. However, it is preferable to use a collimator lens 3 having small aberration in order to reduce the loss of light.

Furthermore, although the aperture and focal length of the collimator lens 3 are limited to three types, respectively, in said embodiment, it may be possible to use various collimator lenses having any aperture and focal length in accordance with the application of the inspection apparatus. However, it is preferable to use a collimator lens having a range of F 4–F 15, for example, for detecting marks or the like formed on a surface of a object such as a semiconductor wafer.

In addition, although the case for inspecting a plate-shaped sample 4 is described in said embodiment, inspection of a cylindrical sample as well as a spherical sample may be possible by irradiating the surface of the sample perpendicularly thereto with the use of a cylindrical lens for the inspection of the cylindrical sample and of a plano-convex lens for the inspection of the spherical sample. In a certain case, it may be also possible to use the cylindrical lens for the inspection of the plate-shaped sample 4 by emphasizing the irregularlity condition in a special direction.

In addition, although the plate-shaped beam splitter is used as the wedge-type half mirror 5 in said embodiment, it may be possible to use various types of half mirrors of a plate-shape or a thin film, for example, a pellicle mirror.

Furthermore, it may be possible to arrange a lattice filter between the half mirror 5 and the aperture stop 61 of the camera lens 62. This lattice filter has grooves in the form of stripe shape, and has a function of diffraction. Light scattered by this lattice filter with a relatively large scattered angle is directed to the aperture of the aperture stop 61. For achieving a similar object, it may be possible to arrange the aperture stop 61 (and the CCD 64, if necessary) at a position eccentric to the optical axis.

Figure 6:
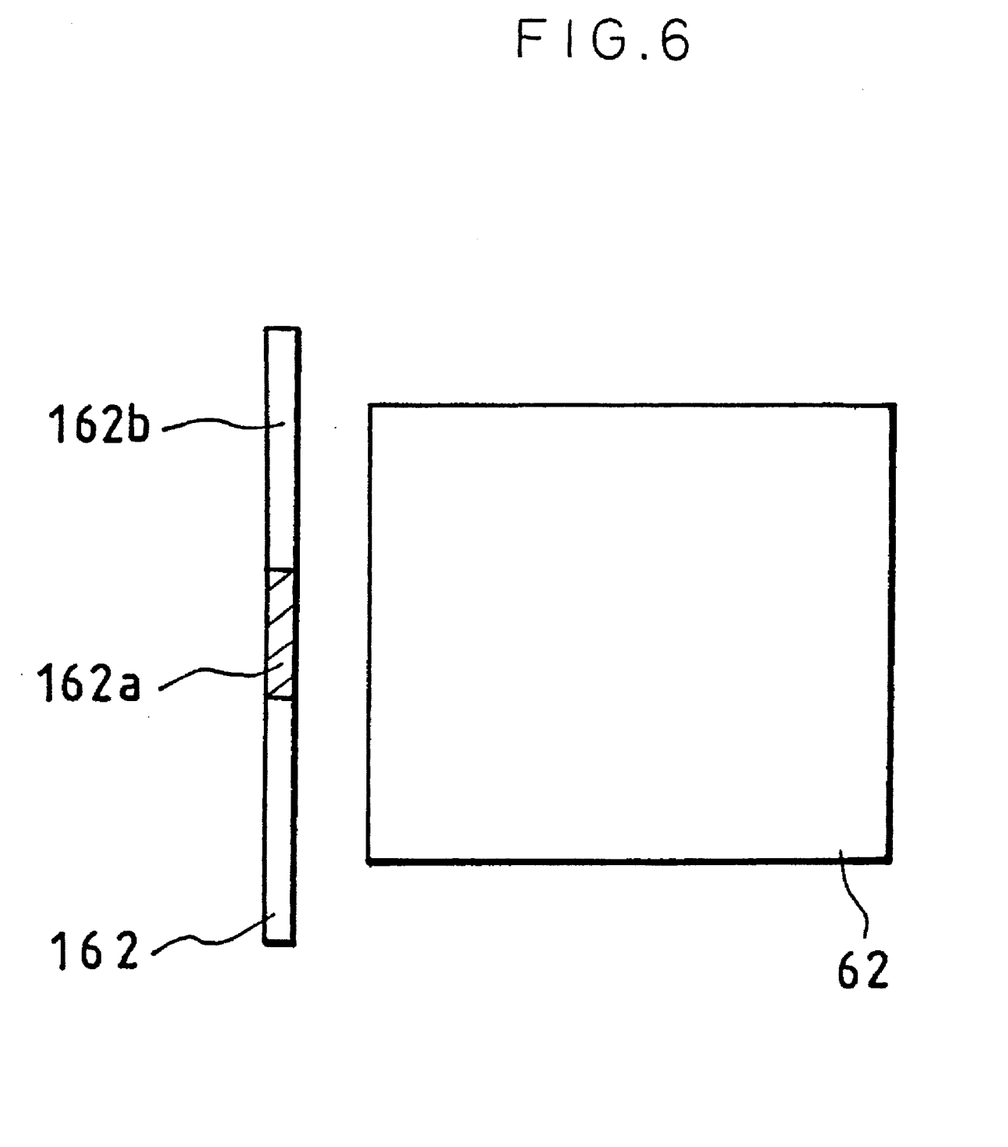
FIG. 6 is a schematic view of a modified embodiment of the detecting apparatus of FIG. 1.

In addition, it may be possible to arrange a peripheral transmission filter 162 such as shown in FIG. 6 between the half mirror 5 and the camera lens 62. The peripheral transmission filter 162 has an ND portion 162a at the center thereof, and a transmissible portion at the periphery thereof. Although the incident light to the camera lens 62 includes not only the reflected light from the sample 4 but a luminous point formed by the reflection from the upper surface of the collimator lens 3, it is possible to remove such a luminous point by the ND portion 162a.

Furthermore, although the CCD 64 of 410,000 picture elements is used in said embodiment, it may be possible to use an optical system for observing through a screen, a camera or the naked eye. A phototube such as a photomultiplier may be used in stead of the CCD 64.

Furthermore, it may be possible to have an image indication with being emphasized by a weak contrast difference through a differential processing for differentiating an image signal (an original image signal) contained in a video signal input from the CCD 64 and then for adding thus obtained differential signal and the original image signal to have a new image signal. In addition, it may be possible to provide a luminance control circuit which can freely set the luminance of the added new image signal. With this luminance control, it is possible to observe the image at a best suit luminance for observation, for example, when observing a condition inside the marginal portion such as irregularlities or marginal portion itself.

Furthermore, although the iris stop is used as the aperture stop 61 in said embodiment, it may be possible to provide an aperture stop having a fixed circular aperture formed therein and to make the aperture stop move along the optical axis.

Furthermore, although the aperture stop 61 is arranged at the back focal plane in said embodiment, the position may be set at any position near the back focal plane.

In additions although the camera lens 62 of a zooming type is used in said embodiment, it may be possible to use any lens of a fixed focus type. For example, any commercially available lens for a single-lens reflex camera may be used.

What is claimed is:

1. An apparatus for inspecting the surface condition of an object, comprising:

(A) light irradiating means for irradiating said object;

(B) an optical element having a back focal plane for converging the light reflected by the surface of the object at the back focal plane to form an image behind the back focal plane;

(C) a half mirror having a light reflecting surface and a light transmitting surface forming a predetermined micro angle therebetween for dividing the reflected light from the optical path of the irradiating light by partially reflecting the reflected light by said light reflecting surface;

(D) an aperture stop arranged behind said half mirror and at or near the back focal plane for cutting off a scattered component of the reflected light and ghost light generated by reflection of the reflected light by said light transmitting surface of said half mirror; and (E) observing means arranged behind the back focal plane for observing the image.

2. An apparatus for inspecting the surface condition of an object as claimed in claim 1, wherein said mirror is wedge-shaped.

3. An apparatus for inspecting the surface condition of an object as claimed in claim 2, wherein said angle is 1°.

4. An apparatus for inspecting the surface condition of an object according to claim 1, wherein said aperture stop is an iris diaphragm.

* * * * *